United States Patent [19]
Petrzilka et al.

[11] Patent Number: 4,493,533
[45] Date of Patent: Jan. 15, 1985

[54] IMMERSION OIL CONTAINING ALIPHATIC THIO COMPOUNDS

[75] Inventors: Martin Petrzilka, Kaiseraugst; Inge Pracht, Riehen; Urs Ruf, Biel-Benken, all of Switzerland

[73] Assignee: Hoffmann-La Roche Inc., Nutley, N.J.

[21] Appl. No.: 370,120

[22] Filed: Apr. 20, 1982

[30] Foreign Application Priority Data

Apr. 27, 1981 [CH] Switzerland ................. 2730/81
Jan. 18, 1982 [CH] Switzerland ................. 272/82

[51] Int. Cl.³ .............. C07C 149/18; G02B 1/04; G02B 21/00; C10M 3/32
[52] U.S. Cl. .................................. 350/418; 252/1; 252/408.1; 350/414; 560/103; 560/109; 560/112; 568/45; 568/46
[58] Field of Search .................. 252/408.1, 1; 568/46, 568/45; 560/109, 112, 103; 350/418, 414

[56] References Cited

U.S. PATENT DOCUMENTS

| | | | |
|---|---|---|---|
| 2,582,605 | 1/1952 | Richter et al. | 252/408.1 |
| 3,297,393 | 1/1967 | Ziegler | 350/418 |
| 3,437,402 | 4/1969 | Levins | 350/418 |
| 3,876,288 | 4/1975 | Iwata | 350/418 |
| 3,929,667 | 12/1975 | Bautis | 350/418 |
| 3,979,301 | 9/1976 | Ushioda | 252/408.1 |
| 4,108,794 | 8/1978 | Yonekubo | 350/418 |

FOREIGN PATENT DOCUMENTS

| | | | |
|---|---|---|---|
| 1285749 | 1/1962 | France . | |
| 1575898 | 7/1969 | France . | |
| 48-34723 | 10/1973 | Japan . | |
| 51-41595 | 11/1976 | Japan . | |
| 487323 | 6/1938 | United Kingdom | 568/45 |
| 647911 | 12/1950 | United Kingdom | 568/45 |

OTHER PUBLICATIONS

CA. 62, 16038g.

Primary Examiner—Teddy S. Gron
Attorney, Agent, or Firm—Jon S. Saxe; Bernard S. Leon; Alan R. Stempel

[57] ABSTRACT

Immersion oils containing aliphatic thio compounds are described. The oils have optical properties and are useful in immersion optics such as fluorescence microscopy.

17 Claims, No Drawings

IMMERSION OIL CONTAINING ALIPHATIC THIO COMPOUNDS

BACKGROUND OF THE INVENTION

The term "immersion oil" is a familiar technical term in the field of microscopy and related fields and does not signify oils in the ordinary sense, but embraces general immersion media which are suitable for oil immersion optics. In the field of microscopy, for example, oil immersion optics are used at the objective lens and condenser lens of a microscope. The immersion oil used in oil immersion optics forms a part of the optical system and therefore must be precisely adapted to the optical system.

In oil immersion optics the immersion oil completely fills the space between objective and cover glass or preparation to be investigated. In oil immersion microscopic investigation there is obtained a higher resolution and light intensity as well as a substantially less spherical aberration than in a dry optical system (refractive index $n_D$ of air 1.000) or in a water immersion optical system (refractive index $n_D$ of water 1.332).

In oil immersion microscopy the refractive index $n_D$ of the immersion oil should be adapted at least to the glass of the objective front lens, i.e. should amount to about 1.500 to about 1.525 (at 23° C.). According to agreement of microscope manufacturers and corresponding regulations of the German Institute for Standards, an immersion oil should have the following values: $n_D(23°\ C.)=1.515$, $n_e(23°\ C.)=1.518\pm0.0004$ and dispersion $\nu_e=44\pm5$.

Further, the immersion oil should have good UV-transmissivity, should be as fluorescence-free as possible and should neither affect glass, synthetic object carriers nor most of the samples to be investigated. Moreover, the immersion oil should be colorless, should be as odorless as possible, should not be hygroscopic, should have a viscosity which allows it to be easily handled, should have no harmful effect on the user and should exhibit a constant composition, i.e. no optical change should occur by the influence of light, air, temperature and the like.

The hitherto known immersion oils consist for the most part of mixtures of mineral oils, paraffin oils and/or polyisobutylenes with compounds having a high refractive index such as, for example, polychlorinated biphenyls (PCB) or hydrogenated terphenyls as disclosed in U.S. Pat. No. 3,929,667.

The PCB compounds are known to be toxic and environmentally dangerous and are therefore used only when it is absolutely necessary because of their favorable fluorescence properties. The other compounds such as, for example, the hydrogenated terphenyls have on the other hand the disadvantage of a moderate to slight, but still troublesome fluorescence in UV-light and a worse transmissivity. Moreover, PCB compounds affect synthetic materials such as, for example, synthetic object carriers.

Water-soluble immersion oils have the advantage that the cleaning of the objective and objective carrier is substantially facilitated. On the other hand, in the case of water-soluble immersion oils there exists the danger that coloring substance is dissolved out from noncovered, colored microscopic sections or smear preparations (e.g. blood smears) or insufficiently fixed objects are washed away. In such cases there is therefore advantageously used a non water-soluble immersion oil.

SUMMARY OF THE INVENTION

The present invention relates to aliphatic thio compounds, namely thioglycols and monoesters thereof, for use for immersion oils, a novel immersion oil as well as its use in optics, especially in fluorescence microscopy.

The aliphatic thio compounds are compounds of the formula

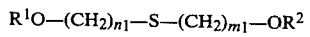

$$R^1O-(CH_2)_{n1}-S-(CH_2)_{m1}-OR^2 \qquad I$$

wherein $R^1$ denotes hydrogen, benzoyl or a group $-(CH_2)_{n2}-OR^3$ and $R^2$ denotes hydrogen or a group $-(CH_2)_{m2}-OR^4$, $R^3$ represents hydrogen or a group $-(CH_2)_{n3}-OH$ and $R^4$ represents hydrogen or a group $-(CH_2)_{m3}-OH$, the indices $n_1$, $m_1$, $n_2$, $m_2$, $n_3$ and $m_3$ signify whole numbers of 2 to 6 and the sums $n_1+m_1$ or $n_2+m_2$ or $n_3+m_3$ amount to at most 8, or derivatives thereof in which one or more of the methylene groups is/are substituted by alkyl groups containing 1 to 4 carbon atoms.

The present invention provides an immersion oil which satisfies the optical requirements and at the same time does not have or has to a lesser extent the disadvantages of the previously known immersion oils. The immersion oils in accordance with the invention can be water-soluble or non water-soluble.

Surprisingly, it has now been found that desired properties for an immersion oil can be achieved with an immersion oil based on aliphatic thio compounds. In particular, it has been shown that aliphatic thio compounds have very good UV-transmissivity, are practically fluorescence free (UV to blue excitation) and are not corrosive towards glass, synthetic materials or to the samples which are most frequently investigated. Naturally, there are preferred those thio compounds which are completely harmless from the point of view of odor and ecotoxicology, particularly 2,2'-thiodiethanol (thiodiethyleneglycol), its benzoid acid monoester and compounds closely related thereto.

DETAILED DESCRIPTION OF THE INVENTION

As used in the present invention the term "thioglycols" means a compound of formula I, which compound contains two hydroxy groups and a thioether group. The following are examples of especially preferred thioglycols:

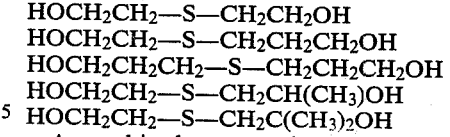

HOCH$_2$CH$_2$—S—CH$_2$CH$_2$OH
HOCH$_2$CH$_2$—S—CH$_2$CH$_2$CH$_2$OH
HOCH$_2$CH$_2$CH$_2$—S—CH$_2$CH$_2$CH$_2$OH
HOCH$_2$CH$_2$—S—CH$_2$CH(CH$_3$)OH
HOCH$_2$CH$_2$—S—CH$_2$C(CH$_3$)$_2$OH

As used in the present invention, the term "monoesters" of thioglycols means a thioglycol as previously defined wherein one of the two hydroxy groups therein is replaced with the benzoyloxy group. An especially preferred example of the monoester thioglycol is the compound of formula:

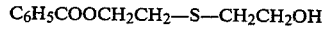

$$C_6H_5COOCH_2CH_2-S-CH_2CH_2OH$$

Fluorescence-free means that the fluorescence of the immersion oil in a horizontal quartz cuvette of 0.2 mm layer thickness in the quantitative measurement in a fluorescence microscope is not significantly different from water. Depending on the nature of the additive and the purity of the components the immersion oils in accordance with the invention exhibit no fluorescence or only a very slight fluorescence.

Immersion oils based on the thio compounds of formula I in which $R^1$ represents hydrogen or a group $-(CH_2)_{n2}-OR^3$ (i.e. aliphatic thioglycols) are water-soluble, and immersion oils based on the thio compounds of formula I in which $R^1$ denotes benzoyl (i.e. thioglycol monoesters) are non water-soluble.

The refractive index $n_D$ of the immersion oils in accordance with the invention conveniently amounts at 23° C. to about 1.500 to about 1.525, preferably about 1.515.

Depending on the purpose of use the refractive index of the immersion oil can be optimized by conventional procedures to the desired value by the addition of suitable compounds having a lower or higher refractive index. Such additives are basically known and may be added to the immersion oil in any effective amounts. Examples of preferred additives for increasing the refractive index are 2-(hydroxymethyl)thiophene ($n_D$=1.562) or for water-miscible immersion oils also 2-hydroxyethyl-disulphide ($n_D$=1.565). Examples of preferred additives for lowering (decreasing) the refractive index are for water-miscible immersion oils aliphatic glycols (e.g. polyethyleneglycol and 2-alkyl-1,3-propanediols), 1,3-dimethoxy-2-propanol ($n_D$=1.418) and alkanols containing 1 to 10 carbon atoms and for non water-miscible immersion oils lycopane ($n_D$=1.458), isophytol ($n_D$=1.455), 1,2,3-trimethoxypropane ($n_D$=1.402), 1,3-dimethoxy-2-propanol ($n_D$=1.418), phythyl methyl ether ($n_D$=1.453) and alkanols containing 11 to 20 carbon atoms.

Isophytol is especially suitable for lowering the refractive index for non water-miscible immersion oils and aliphatic glycols, for example the polyethyleneglycols of various degrees of polymerization are suitable for lowering the refractive index for water-miscible immersion oils. Depending on the desired viscosity and desired temperature range there are generally used polyethyleneglycols of different degrees of polymerization (average molecular weight conveniently between about 200 and about 10,000).

For example 2,2'-thiodiethanol (thiodiethyleneglycol), which is the most preferred thioglycol, has a refractive index of $n_D^{23}$=1.5203, which can be lowered readily, for example by the addition of polyethyleneglycol.

Of the thio compounds defined earlier there are preferred those in which $R^3$ or $R^4$, preferably both symbols, signify hydrogen. Especially preferred are those compounds in which $R^2$ and $R^3$ signify hydrogen and especially those in which $R^1$ signifies hydrogen or benzoyl and $R^2$ signifies hydrogen. The sum $n_1+m_1$ or $n_2+m_2$ or $n_3+m_3$ preferably amount to at most 6 (i.e., where in each case both groups in question are present in sums amounting to 4 to 6). Of the thio compounds used in accordance with the invention there are further preferred those which contain at most two alkyl groups. The methyl group is the preferred alkyl group. Furthermore, the non-alkyl-substituted compounds, i.e. the compounds of formula I, are preferred over the alkyl-substituted thio compounds.

Quite especially preferred thio compounds are therefore those compounds of formula I in which $R^1$ denotes hydrogen or benzoyl, $R^2$ signifies hydrogen and the sum $n_1+m_1$ amounts to 4 to 6, as well as their methyl and dimethyl derivatives. Most important representatives of such compounds are 2,2'-thiodiethanol (thiodiethyleneglycol) and 2-[(2-hydroxyethyl)thio]ethyl benzoate.

The thio compounds can basically be present in the immersion oils in accordance with the invention in any amount. The amount of additives optionally present is determined by the purpose of use and especially by the desired refractive index. However, in general it should be endeavored to use an amount of thio compound which is as high as possible. Conveniently, the amount of thio compounds in which $R^1$ denotes hydrogen or a group $-(CH_2)_{n2}-OR^3$ in the water-soluble immersion oils in accordance with the invention therefore amounts to at least about 50 percent by weight, preferably at least about 70 percent by weight. The non water-soluble immersion oils conveniently contain at least about 40 percent by weight, preferably at least about 50 percent by weight of thio compounds in which $R^1$ signifies benzoyl. Of course, the present invention also embraces immersion oils which contain only thio compounds.

The manufacture of the immersion oils consisting of two or more components and the optimization of the refractive index can be carried out in a manner known per se; for example, by mixing the approximate amounts of the components at an elevated temperature, cooling the mixture, measuring the refractive index and, if desired, adding the appropriate component (or components) until the desired refractive index is attained.

The odor which frequently accompanies the commercially obtainable compounds can generally be readily removed by usual purification procedures, for example chromatography and/or distillation.

The immersion oils in accordance with the invention can be used in various fields of optics. For example, on the basis of their high transmissivity they can be used in place of immersion glycerine and in absorption photometry. Other related fields of use are: as optical standard substances, liquid carrier media, optical coupling media (glass fibre optics) and as transparent investigation fluids for the establishment of differences in materials (e.g. testing of contact lenses or in the electronic industry). However, the preferred field of use is microscopy and especially fluorescence microscopy.

The use of the present invention in oil immersion optics can be by any means or methods known per se for the use of oil immersion in oil immersion optics.

The present invention is further concerned with all novel compounds, mixtures, processes, uses and devices as herein described.

The present invention is illustrated further by the following Examples but these Examples are not meant to limit the present invention in scope or spirit. The fluorescence measurement in the Examples was determined in quarts cuvettes of 0.2 mm layer thickness with a microscope fluorometer for the three excitations UV, violet and blue. The relative fluorescence was ascertained by comparison with water (0%) and a glass standard (100%).

EXAMPLE 1

About 90 parts by weight of 2,2'-thiodiethanol (thiodiethyleneglycol, purity at least 99%) and about 10 parts by weight of polyethyleneglycol (with an average molecular weight of about 1000; purest quality) are mixed while warming until a clear, homogeneous fluid is obtained. After cooling to 23° C., the refractive index $n_D$ of the fluid is monitored and, if necessary, adjusted precisely by further addition of one of the two components.

The immersion oil obtained is colorless, almost odorless, water-miscible, not corrosive towards glass and synthetic object carriers and has the following technical properties:

| | |
|---|---|
| Refractive index at 23° C. | $n_F$ (486.10 nm) = 1.523 |
| | $n_e$ (546.07 nm) = 1.518 |
| | $n_D$ (589.26 nm) = 1.515 |
| | $n_C$ (656.30 nm) = 1.512 |
| Temperature dependence of the refractive index (18–30° C.) | $\Delta n/\Delta T$ = 0.00035/°C. |
| Dispersion (Abbe) | $\nu_e$ = 45 |
| Fluorescence (UV violet and blue excitation) | not different from distilled water in the microscope |
| Density at 23° C. | 1.18 g/ml |
| Viscosity at 23° C. | 74.0 mPa.s |
| Turbidity point | about −20° C. |
| Spectral transmissivity $\tau_i$ (0.2 mm layer thickness) | 50% at about 260 nm, >95% at 330 nm |

EXAMPLE 2

In an analogous manner to Example 1, about 60 parts by weight of 2-[(2-hydroxyethyl)thio]ethyl benzoate and about 40 parts by weight of isophytol are mixed and then the refractive index $n_D$ of the resulting mixture is adjusted precisely.

The immersion oil obtained is colorless, almost odorless, non water-miscible, nonhygroscopic, noncorrosive towards glass, synthetic object carriers and blood smears and has the following additional properties:

| | |
|---|---|
| Refractive index at 23° C. | $n_F$ (486.10 nm) = 1.525 |
| | $n_e$ (546.07 nm) = 1.518 |
| | $n_D$ (589.26 nm) = 1.515 |
| | $n_C$ (656.30 nm) = 1.511 |
| Temperature dependence of the refractive index (18–30° C.) | $\Delta n/\Delta T$ = 0.00038/°C. |
| Dispersion (Abbe) | $\nu_e$ = 37 |
| Density at 23° C. | 1.05 g/ml |
| Viscosity at 23° C. | 72 mPa.s |
| Spectral transmissivity $\tau_i$ 0.2 nm layer thickness | 50% at about 300 nm, >95% at 330 nm |
| Relative fluorescence | 9% for UV excitation, 3% for violet excitation, 3% for blue excitation (standard deviation 1.9%) |

EXAMPLE 3

The following mixtures are manufactured in an analogous manner to Example 1:

(a) About 90 parts by weight of 2,2'-thiodiethanol (thiodiethyleneglycol) and about 10 parts by weight of polyethyleneglycol 4000 are mixed to provide a colorless, water-miscible mixture having a refractive index $n_D^{23}$=1.515; fluorescence for UV, violet and blue excitation not different from distilled water in the microscope.

(b) About 70 parts by weight of 2,2'-thiodiethanol (thiodiethyleneglycol) and about 30 parts by weight of 4-[(2-hydroxyethyl)thio]-2-methyl-2-butanol are mixed to provide a colorless, water-miscible mixture having refractive index $n_D^{23}$=1.515; fluorescence for violet and blue excitation not different from distilled water in the microscope; relative fluorescence for UV excitation 5.7 percent (standard deviation 1.9 percent).

EXAMPLE 4

2.55 g of lithium aluminum hydride are suspended in 100 ml of absolute tetrahydrofuran under argon gasification and treated with a warm solution of 12.0 g of 3,3'-thiodipropionic acid in 100 ml of absolute tetrahydrofuran. After completion of the addition, the resulting heterogenous mixture is heated to reflux for a further 22 hours. After cooling, the mixture is treated with 12.0 ml of saturated potassium carbonate solution, filtered and concentrated. Low-pressure chromatography (0.4 bar) of the resulting colorless oil on silica gel with ethyl acetate and subsequent bulb-tube distillation (150°–170° C./0.15–0.09 mm Hg) gives 2.0 g of 3,3'-thiodi-1-propanol as a colorless, viscous oil; $n_D^{23}$=1.5088; relative fluorescence: 20 percent for UV excitation, 2 percent for violet excitation, 5 percent for blue excitation.

EXAMPLE 5

(a) A mixture of 14.0 ml of mercaptoethanol and 0.15 ml of a 40 percent solution of Triton B in methanol is placed under argon gasification and treated dropwise while cooling with ice during 40 minutes with 36.6 ml of methyl acrylate (the internal temperature should not exceed 25° C.). After completion of the addition, the mixture is stirred at room temperature for a further 19 hours, then excess methyl acrylate is distilled off and the residual oil is distilled. In the main run (b.p. 157°–161° C./12 mm Hg) there are obtained 22.0 g (67 percent) of 3-[(2-hydroxyethyl)thio]-propionic acid methyl ester as a colorless liquid.

(b) 1.15 g of lithium aluminum hydride are suspended in 50 ml of absolute tetrahydrofuran under argon gasification and treated within 15 minutes with a solution of 5.0 g of 3-[(2-hydroxyethyl)thio]propionic acid methyl ester in 50 ml of absolute tetrahydrofuran. After completion of the addition, the resulting heterogeneous mixture is heated to reflux for a further 3 hours. After cooling, the mixture is treated with about 5.0 ml of saturated potassium carbonate solution, filtered and the filtrate is concentrated. Bulb-tube distillation (150° C./0.25–0.15 mm Hg) of the residue (4.18 g) gives 3.52 g (86 percent) of 3-[(2-hydroxyethyl)thio]-1-propanol as a colorless unpleasantly smelling oil; $n_D^{23}$=1.5139. In order to remove the odor, this material is further purified by low-pressure chromatography (0.5 bar) on silica gel with ethyl acetate and subsequent bulb-tube distillation (150° C./0.17–0.20 mm Hg). There are obtained 3.07 g (75 percent) of 3-[(2-hydroxyethyl)thio]-1-propanol as a viscous, odorless oil; $n_D^{23}$=1.5139; relative fluorescence: 13 percent for UV excitation, 4 percent for violet excitation, 4 percent for blue excitation.

EXAMPLE 6

100 ml of a 1N solution of methylmagnesium bromide in diethyl ether are placed under argon gasification and treated dropwise with a solution of 5.0 g of 3-[(2-hydroxyethyl)thio]propionic acid methyl ester (prepared according to Example 5) in 25 ml of diethyl ether so that a slight reflux results. After completion of the addition, the resulting mixture is stirred at room temperature for a further 16 hours. Subsequently, the excess Grignard reagent is destroyed by the cautious addition of saturated ammonium chloride solution to the mixture and the mixture is extracted three times with 100 ml of methylene chloride each time. The organic phases are dried over magnesium sulfate and concentrated. Low-pressure chromatography (0.4 bar) of the residue on silica gel with ethyl acetate and subsequent bulb-tube distillation (150° C./0.23–0.18 mm Hg) gives 2.25 g (46 percent) of 4-[(2-hydroxyethyl)thio]-2-methyl-2-butanol as a viscous, colorless oil; $n_D^{23} = 1.5027$.

EXAMPLE 7

A solution of 8.5 ml of 2,2'-thiodiethanol (thiodiethyleneglycol) in 100 ml of pyridine is placed at −5° C. under argon gasification and treated dropwise within 10 minutes with 9.5 ml of benzoyl chloride. Thereby, the resulting mixture warms to about +8° C. and towards the end of the addition white crystals begin to precipitate. Subsequently, the mixture is stirred at room temperature for a further 36 hours and then the majority of the pyridine is distilled off on a rotary evaporator. The semicrystalline residue is added to 100 ml of ice-cold 2N hydrochloric acid and extracted three times with 100 ml of diethyl ether each time. The organic phases are washed twice with 100 ml of water each time and once with 100 ml of saturated sodium chloride solution, dried over magnesium sulfate and concentrated. Low-pressure chromatography (0.5 bar) of the residue (about 14 g) on silica gel with the use of toluene/ethyl acetate (3:1) as the elution agent gives in succession 1.5 g (5.5 percent) of crystalline dibenzoate and 11 g (59 percent) of 2-[(2-hydroxyethyl)thio]ethyl benzoate as a colorless, viscous oil. After bulb-tube distillation (160°–170° C./0.20–0.16 mm Hg) of the latter, there are obtained 9.7 g (52.4 percent) of 2-[(2-hydroxyethyl)thio]ethyl benzoate in 99.4 percent purity; $n_D^{23} = 1.5566$.

We claim:

1. In the combination for immersion oil optics of an immersion oil completely filling the space between the objective lens and a preparation or a cover glass over the preparation to be optically investigated, the improvement wherein the optical immersion oil comprises one or more aliphatic thio compounds of the formula $$R^1O-(CH_2)_{n_1}-S-(CH_2)_{m_1}-OR^2 \qquad I$$

wherein $R^1$ denotes hydrogen, benzoyl or a group $-(CH_2)_{n_2}-OR^3$ and $R^2$ denotes hydrogen or a group $-(CH_2)_{m_2}-OR^4$, $R^3$ represents hydrogen or a group $-(CH_2)_{n_3}-OH$ and $R^4$ represents hydrogen or a group $-(CH_2)_{m_3}-OH$, the indices $n_1$, $m_1$, $n_2$, $m_2$, $n_3$ and $m_3$ signify whole numbers of 2 to 6 and the sums $n_1+m_1$ or $n_2+m_2$ or $n_3+m_3$ amount to at most 8, or derivatives thereof in which one or more of the methylene groups is/are substituted by alkyl groups containing 1 to 4 carbon atoms.

2. In the improved oil according to claim 1 the immersion oil wherein $R^1$ represents hydrogen or a group $-(CH_2)_{n_2}-OR^3$, wherein n and $R^3$ are as defined in claim 1, said immersion oil being water-soluble.

3. In the improved oil according to claim 1 the immersion oil wherein $R^1$ represents benzoyl, said immersion oil being non water-soluble.

4. In the improved combination according to claim 1 the immersion oil wherein the refractive index $n_D$ of the immersion oil at 23° C. amounts to about 1.500 to about 1.525.

5. In the improved combination according to claim 4 the immersion oil wherein the refractive index $n_D$ at 23° C. amounts to about 1.515.

6. In the improved combination according to claim 1 the immersion oil wherein $R^3$ and $R^4$ represent hydrogen.

7. In the improved combination according to claim 1 the immersion oil wherein $R^1$ represents hydrogen, benzoyl or a group $-(CH_2)_{n_2}-OR^3$ and $R^2$ and $R^3$ represent hydrogen and $n_2$ is as defined claim 1.

8. In the improved combination according to claim 7 the immersion oil wherein $R^1$ represents hydrogen or benzoyl and $R^2$ represents hydrogen.

9. In the improved combination according to claim 1 the immersion oil wherein the sums $n_1+m_1$ or $n_2+m_2$ or $n_3+m_3$ amount to at most 6.

10. In the improved combination according to claim 1 the immersion oil wherein the compound of formula I contains at most two alkyl groups.

11. In the improved combination according to claim 1 the immersion oil wherein the alkyl groups are methyl groups.

12. In the improved combination according to claim 1 the immersion oil wherein $R^1$ denotes hydrogen or benzoyl, $R^2$ signifies hydrogen and the sum $n_1+m_1$ amounts to 4 to 6 and the alkyl groups are methyl or dimethyl.

13. In the improved combination according to claim 12 the immersion oil comprising 2,2'-thiodiethanol or 2-[(2-hydroxyethyl)thio]ethyl benzoate.

14. In the improved combination according to claim 1 further the immersion oil comprising additives for increasing or decreasing the refractive index of the immersion oil.

15. In the improved combination according to claim 14 the immersion oil wherein the additives are selected from the group consisting of aliphatic glycols and alkanols containing 1 to 20 carbon atoms.

16. In the improved combination according to claim 15 the immersion oil comprising 2,2'-thiodiethanol and polyethyleneglycol, said immersion oil being water-soluble.

17. In the improved combination according to claim 15 the immersion oil comprising 2-[(2-hydroxyethyl)thio]-ethyl benzoate and isophytol, said immersion oil being non water-soluble.

* * * * *